United States Patent
Chen et al.

(10) Patent No.: US 9,535,047 B2
(45) Date of Patent: Jan. 3, 2017

(54) METHOD FOR PROVIDING AN INDICATION AS TO THE AMOUNT OF MILK REMAINING IN A BREAST DURING LACTATION

(71) Applicant: KONINKLIJKE PHILIPS N.V., Eindhoven (NL)

(72) Inventors: Xin Chen, Eindhoven (NL); Xiaoxin Wang, Eindhoven (NL); Renjun Yu, Eindhoven (NL); Huanhuan Zhang, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 157 days.

(21) Appl. No.: 14/367,491

(22) PCT Filed: Dec. 14, 2012

(86) PCT No.: PCT/IB2012/057314
§ 371 (c)(1),
(2) Date: Jun. 20, 2014

(87) PCT Pub. No.: WO2013/093739
PCT Pub. Date: Jun. 27, 2013

(65) Prior Publication Data
US 2015/0051458 A1    Feb. 19, 2015

Related U.S. Application Data

(60) Provisional application No. 61/579,305, filed on Dec. 22, 2011.

(30) Foreign Application Priority Data

Dec. 22, 2011 (EP) .................................. 11195114

(51) Int. Cl.
*A61B 5/1455* (2006.01)
*G01N 33/06* (2006.01)
(Continued)

(52) U.S. Cl.
CPC ............ *G01N 33/06* (2013.01); *A61B 5/0059* (2013.01); *A61B 5/4288* (2013.01);
(Continued)

(58) Field of Classification Search
None
See application file for complete search history.

(56) References Cited

U.S. PATENT DOCUMENTS

| 5,827,191 A | 10/1998 | Rosenfeld |
| 2005/0059928 A1 | 3/2005 | Larsson |

(Continued)

FOREIGN PATENT DOCUMENTS

| EP | 0404207 A2 | 12/1990 |
| GB | 2283091 A | 4/1995 |

(Continued)

OTHER PUBLICATIONS

Daly S.E.J. et al: "Degree of breast emptying explains change in the fat content, but not fatty acid composition, of human milk" Experimental physiology, Cambridge University Press, Cambridge, GB, vol. 78, No. 6, 1 Jan. 1993, pp. 741-755, XP008030117, ISSN: 0958-0670 *Milk fat content and breast volume p. 747-749*.

(Continued)

*Primary Examiner* — Eric Winakur
*Assistant Examiner* — Marjan Fardanesh

(57) ABSTRACT

A method of providing an indication as to the amount of milk remaining in a breast during lactation based on a determined fat content of milk that has been expressed from said breast is disclosed. The method of determining said fat content comprises measuring an optical characteristic of (Continued)

milk following expression and by comparing said measured optical characteristic with data representing a corresponding optical characteristic of a sample of milk having a known fat content to determine the fat content of said expressed milk which is indicative of the amount of milk remaining in the breast.

13 Claims, 2 Drawing Sheets

(51) Int. Cl.
*A61B 5/00* (2006.01)
*A61M 1/06* (2006.01)
*A61B 10/00* (2006.01)
*A61J 13/00* (2006.01)
*G01J 3/50* (2006.01)
*G01N 21/31* (2006.01)
*G01N 21/59* (2006.01)

(52) U.S. Cl.
CPC ........ *A61B 5/4312* (2013.01); *A61B 10/0045* (2013.01); *A61J 13/00* (2013.01); *A61M 1/06* (2013.01); *G01J 3/50* (2013.01); *G01N 21/31* (2013.01); *G01N 21/59* (2013.01); *A61M 2205/3306* (2013.01); *A61M 2205/50* (2013.01); *A61M 2230/00* (2013.01); *G01N 2201/0612* (2013.01)

(56) References Cited

U.S. PATENT DOCUMENTS

| | | |
|---|---|---|
| 2007/0020357 A1 | 1/2007 | Uni et al. |
| 2011/0004154 A1 | 1/2011 | Van Schijndel et al. |

FOREIGN PATENT DOCUMENTS

| | | |
|---|---|---|
| WO | 0005971 A1 | 2/2000 |
| WO | 0057934 A1 | 10/2000 |
| WO | 0066195 A1 | 11/2000 |
| WO | 0154488 A1 | 8/2001 |
| WO | 2004086980 A1 | 10/2004 |
| WO | 2005016409 A2 | 2/2005 |
| WO | 2009060448 A2 | 5/2009 |
| WO | 2010038184 A1 | 4/2010 |

OTHER PUBLICATIONS

Daly, S. E. J., Kent, J. C., Huynh, D. Q., Owens, R. A., Alexander, B. F., NG, K. C. & Hartmann, P. E. (1992). The determination of short-term breast volume changes and the rate of synthesis of human milk using computerized breast measurement. Experimental Physiology 77, 79-87.

Dorea JG, Homer MR, Bezerra VL, Campanate ML.(Dec. 1982), Variation in major constituents of fore- and hindmilk of Brazilian women, J Trop Pediatr. ;28(6)303-5, Dec. 1982.

Optical measurement of in-process fluids, (McNab, Incorporated, 20 North MacQuesten Parkway, Mount Vernon, New York, USA) 2004.

METHOD FOR PROVIDING AN INDICATION AS TO THE AMOUNT OF MILK REMAINING IN A BREAST DURING LACTATION

This application is the U.S. National Phase application under 35 U.S.C. §371 of International Application No. PCT/IB2012/057314, filed on Dec. 14, 2012 which claims benefit of U.S. Provisional Application No. 61/579,305 filed Dec. 22, 2011 and European Patent Application No. 11195114.1, filed Dec. 22, 2011. This application is hereby incorporated by reference herein.

FIELD OF THE INVENTION

This invention relates to a method of providing an indication as to the amount of milk remaining in a breast during lactation based on a determined fat content of milk that has been expressed from the breast. The invention also relates to a unit for carrying out the method that is attachable to a breast pump and, to a breast pump incorporating such a unit.

BACKGROUND OF THE INVENTION

Exclusive breastfeeding of newborn babies is recommended up to 6 months of age by the World Health Organisation, with continued breastfeeding along with appropriate complementary foods up to two years of age or beyond. It is very important that the mother can produce an appropriate amount of milk for her baby to feed on. This requires good control of the supply-and-demand relationship because the mother's breasts will act to match the amount of milk produced depending on how much the baby feeds.

When a good supply-and-demand relationship is established, the mother's milk supply is matched to the baby's demand. So a normal breastfeeding session will end when the baby has had enough milk. Some mothers choose to express milk with a breast pump when they cannot feed their babies directly or it is inconvenient to do so.

When using a breast pump, it is difficult for the mother to know how much milk remains in her breast and when to stop using the breast pump. It is important to know whether all the milk has been expressed from the breast because, according to lactation physiology, if the breast is not emptied, long term milk production will decrease as the breast acts to balance the supply-and-demand relationship. Furthermore, mastitis may occur if milk remains in the breasts too long, since it creates a good environment for bacterial growth.

It is known that a mother can monitor how much milk is produced and match this to the baby's needs. However, this can be difficult, especially as the baby grows and requires more milk, and the breasts may be caused to produce more or less milk than required.

It is also known, for example from WO 2001/054488 A1, to use flow meters to monitor the rate at which milk is being expressed by a breast pump. This can be used to give an indication of the emptiness of the breasts; the rate will decrease as the breasts empty. However, this may be inaccurate and could confuse breast pump equipment malfunction (such as blockages or loss of vacuum seal) with an empty or almost empty breast.

It is also known, from WO 2009/060448 A2 and US 2005/0059928 A1, to use electronic sensors to monitor the breast during pumping or feeding; the breast's shape, electrical conductivity and other characteristics can give an indication of the fullness of the breasts. Again, this can be inaccurate and is difficult to calibrate for different users.

Furthermore, the methods and devices mentioned above are inconvenient to use and are often bulky and uncomfortable because of the required sensors that are attached in the breast area.

The constitution of milk varies for people, at different lactation stages and even during one breastfeeding. Generally speaking, breast milk is a solution with 87%~88% water, ~4% fat, ~7% lactose and ~1% protein and other minerals. The fat is insoluble in water and so takes the form of fat globules suspended in the water. The fat globules have an average diameter of 4 µm. These are the largest particles present in breast milk. Proteins, such as casein protein, are also present in particle form, but much smaller 0.005 µm-0.3 µm. Other constituents of the breast milk are dissolved in the water and so have no significant particle presence.

It is known that as a breast empties, the fat content of the breast milk rises. The difference in fat content during a breast feeding session can range from 20 gram/liter in foremilk to 130 gram/liter in hindmilk. Typically, scientists use this measure as an accurate and reliable way to determine the amount of milk, if any, remaining in a breast. To determine the fat content of a milk sample, a centrifuge is commonly used to separate the fat (which is insoluble) from the water. The quantity of fat can then be measured.

Another method of determining when a breast is empty is to estimate the breast volume using a breast imaging technique. The shape of the breasts will naturally change as they are emptied and this is a difference visible from the exterior.

Neither the centrifuge nor the breast imaging methods are suitable for regular, everyday use as they require equipment and processes that are complex, costly and inconvenient and which cannot be carried out quickly and easily in real time and on a sample of milk that has only just been expressed from the breast and whilst the breast pump is still in use.

Therefore, there is a need for a method that will quickly and easily provide an indication as to the amount of milk remaining in a breast during lactation, without compromising the function of the breast pump or the comfort and convenience of the user.

SUMMARY OF THE INVENTION

According to the invention, there is provided a method of providing an indication as to the amount of milk remaining in a breast during lactation based on a determined fat content of milk that has been expressed from said breast, wherein the method of determining said fat content comprises measuring an optical characteristic of milk during expression and by comparing said measured optical characteristic with data representing a corresponding optical characteristic of a sample of milk having a known fat content to determine the fat content of said expressed milk, and determining an indication of the amount of milk remaining in the breast from the determined fat content of said expressed milk.

Preferably, the method includes the step of applying an algorithm to determine the fat content of expressed milk based on said comparison of the measured optical characteristic and said corresponding optical characteristic of a sample of milk having a known fat content to determine the fat content of said expressed milk.

As the color of breast milk changes during a breast feeding session due to its fat content, in one embodiment, the step of measuring an optical characteristic of the expressed milk comprises the step of illuminating a portion of milk using a light source and using an RGB sensor to detect the color of the expressed milk and subsequently comparing said measured color with the color of a sample of milk having a known fat content to determine the fat content of said expressed milk which is indicative of the amount of milk remaining in the breast.

In another embodiment, the step of measuring an optical characteristic of the expressed milk comprises the step of illuminating milk following expression using a light source and using a sensor to detect the amount of light that is absorbed by said expressed milk, and subsequently comparing said measured absorption with data representing the absorption of a sample of milk having a known fat content to determine the fat content of said expressed milk which is indicative of the amount of milk remaining in the breast.

Preferably, in this embodiment, the step of using a sensor to detect the amount of light that is absorbed by the expressed milk comprises the step of illuminating the expressed milk with light of a predetermined wavelength and which is known to be scattered or absorbed by globules of fat contained in expressed milk, detecting the amount of light transmitted through said milk and comparing said measured amount of transmitted light with data representing the amount of light transmitted through a sample of milk having a known fat content to determine the fat content of said expressed milk which is indicative of the amount of milk remaining in the breast.

This embodiment may further include the step of illuminating a portion of expressed milk with multiple light sources that emit light of different wavelengths and using multiple sensors to detect the amount of light of each wavelength that is transmitted through the expressed milk, and comparing said measured amount of transmitted light with the amount of light transmitted through a sample of milk having a known fat content to determine the fat content of said expressed milk which is indicative of the amount of milk remaining in the breast.

In yet another embodiment, the step of measuring an optical characteristic of the expressed milk comprises the step of illuminating a portion of expressed milk using a light source and using a sensor to detect attenuation of the light by said expressed milk, and subsequently comparing said measured attenuation with data representing the attenuation of a sample of milk having a known fat content to determine the fat content of said expressed milk which is indicative of the amount of milk remaining in the breast.

In this embodiment, multiple sensors may be used to detect light transmitted through the expressed milk and light which is scattered by said expressed milk and comparing the detected light with light received by a control detector that has not been incident on the expressed milk.

This embodiment may include a beam splitter positioned in the path of the light emitted from the light source such that a portion of the light emitted therefrom towards the expressed milk is directed towards the control detector.

Preferably, the method includes the step of informing the user of the determined fat content of the expressed milk or other indicia representative of the amount of milk remaining in said breast based on the determined fat content, such that the user may control pumping in dependence on said information.

This has the advantage of allowing the user to take control of the supply-and-demand relationship and ensure that sufficient milk is expressed with each use of the breast pump and sensors.

The method may further comprise the step of supplying a signal representative of the determined fat content of the expressed milk to a control unit, said control unit being operable to automatically control pumping in dependence on said signal.

This gives the advantage of being able to set the breast pump to empty the breast and the breast pump will continue to pump until the breast is empty. This ability to automatically stop operation of the pump prevents over-pumping which may be painful and damaging to the breast tissue.

According to another aspect of the invention, there is also provided a device for providing an indication as to the amount of milk remaining in a breast during lactation based on a determined fat content of milk that has been expressed from said breast, said device being releasably attachable to a breast pump and operable to measure an optical characteristic of milk as it is expressed from a breast and for comparing said measured optical characteristic with a corresponding optical characteristic of a sample of milk having a known fat content to determine the fat content of said expressed milk and determine an indication of the amount of milk remaining in the breast from the determined fat content of said expressed milk.

A breast pump may be provided which comprises the unit. Preferably, the breast pump comprises a breast shield for insertion of a breast into the breast pump during use, said unit being releasably attachable to said breast shield.

The breast shield may have a bulge or recess therein to receive and temporarily retain or buffer a sample of milk, said unit being operable to measure an optical characteristic of the milk in said bulge or recess when said unit is attached to said breast pump.

BRIEF DESCRIPTION OF THE DRAWINGS

Preferred embodiments will now be described, by way of example only, with reference to the accompanying drawings, in which.

DETAILED DESCRIPTION

Fat influences the optical characteristics of the milk because of the reflection, absorption and scattering of the light, caused by the fat globules suspended in water. One of the results of this is a change in color of the breast milk as the fat content changes.

Figure 1:
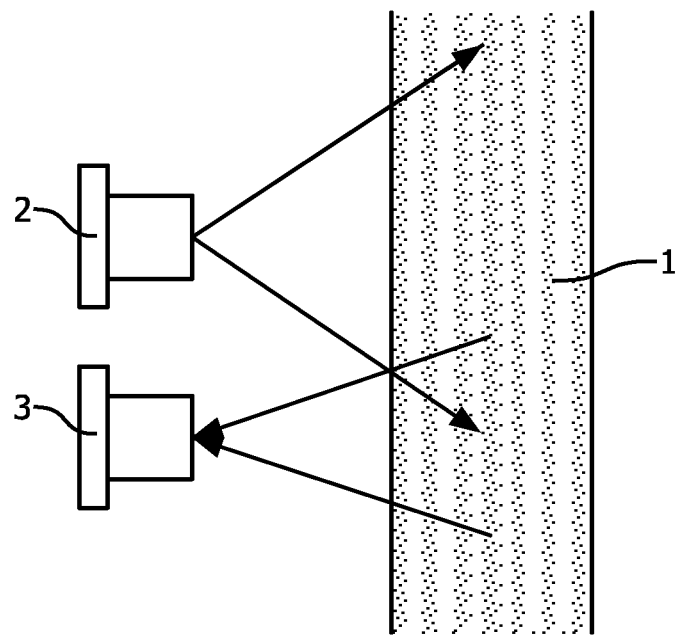
FIG. 1 shows a method drawing of a light source and an optical sensor adjacent to a fluid flow.

Referring to the drawings, FIG. 1 shows a light source 2, an optical sensor 3 and fluid flow 1. The fluid flow 1 represents breast milk that has just been expressed from a breast and has entered a breast pump (not shown). In this embodiment, the light source 2 may be any electrical device that can produce the required light, such as a white (broad spectrum) LED. The optical sensor 3 is configured to detect the color composition of the light after it has been reflected by the fluid flow 1 and can be any type of color sensing element, such as an RGB sensor which outputs numerical data relating to the composition of the color in terms of the red, green and blue elements of the light. The output signal from the optical sensor 3 is transmitted to a control unit (not shown), which compares the signal to known data and informs the user as to the amount of milk remaining in their breast based on the data comparison, thereby enabling them to vary pumping accordingly. Alternatively, the breast pump may be controlled automatically in dependence on the output from the sensor 3 and comparison with known data.

In the embodiment of FIG. 1, the light source 2 and the optical sensor 3 are shown as separate parts and are positioned alongside the fluid flow, adjacent to each other. However, it will be appreciated that the light source 2 and optical sensor 3 might be arranged differently, anywhere in the area around the fluid flow 1, and may even be combined into one component with a dual function of emitting light and detecting the color of the fluid flow.

Figure 2:
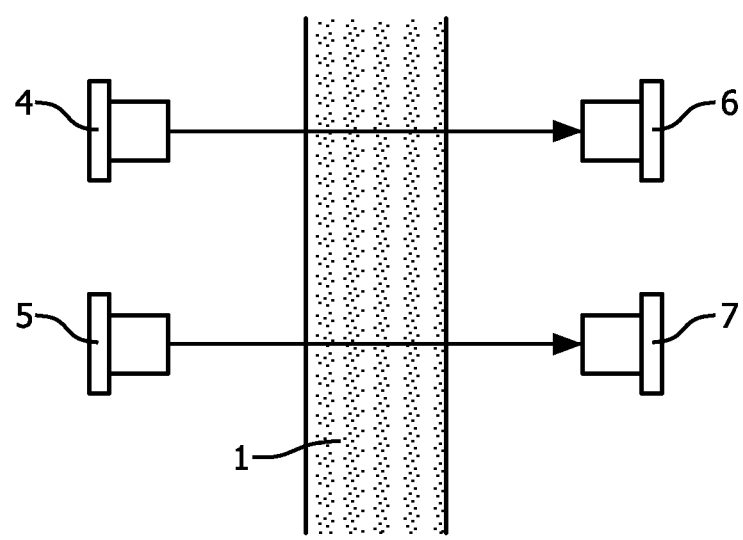
FIG. 2 shows a method of using a pair of light sources and a corresponding pair of optical sensors located on opposite sides of a fluid flow.

FIG. 2 shows another embodiment of the method comprising two light sources 4, 5 with two optical sensors 6, 7 positioned on an opposite side of the fluid flow 1 from the light sources 4, 5. The light sources 4, 5 produce light, with a controlled wavelength respectively, directed towards the fluid flow 1. The optical sensors 6, 7, positioned on the opposite side of the fluid flow 1, detect the light after it has passed through the fluid flow 1. It is configured such that the first optical sensor 6 exclusively detects light from the first light source 4, and the second optical sensor 7 exclusively detects light from the second light source 5. The fluid flow 1 is representative of breast milk that has just been expressed from a breast and has entered a breast pump (not shown).

In this embodiment, it is important to control the wavelengths of the light emitted by the light sources so that they are particularly vulnerable to absorption or scattering by the fat globules in the breast milk, but avoid, as much as possible, scattering by other constituents of the breast milk. As previously mentioned, the fat globules are typically 1.5 µm-12 µm in diameter, with an average of 4.5 µm. Breast milk also contains casein protein particles which can scatter or absorb light. However, casein particles cannot be used to give an indication of the emptiness of the breasts because the percentage casein content of breast milk is fairly constant throughout a feeding session.

With this knowledge, the wavelengths of the light emitted from the light sources 4, 5 can be selected such that the absorption and scattering caused by the fat globules can be distinguished from the absorption and scattering caused by the casein particles.

The first and second light sources 4, 5 comprise laser diodes and the first and second optical sensors 6, 7 comprise photodiodes. The first and second laser diodes 4, 5 emit light of different wavelengths to increase the reliability of the readings and account for the variation in fat globule size.

As the light created by the first and second laser diodes 4, 5 passes through the breast milk 1, some of the light is absorbed by the fat, protein and other constituents of the breast milk 1. The first and second photodiodes 6, 7 detect the light, after it has been altered by the breast milk 1, and in cooperation with a control unit (not shown); can identify the amount of light that has been absorbed by the fat globules in the breast milk 1. The control unit can compare the measurements to empirical results and use an algorithm to determine the fat content of the breast milk. This information can be used to detect the amount of milk remaining in the breast and inform the user or actuate some control action in the breast pump.

Figure 3:
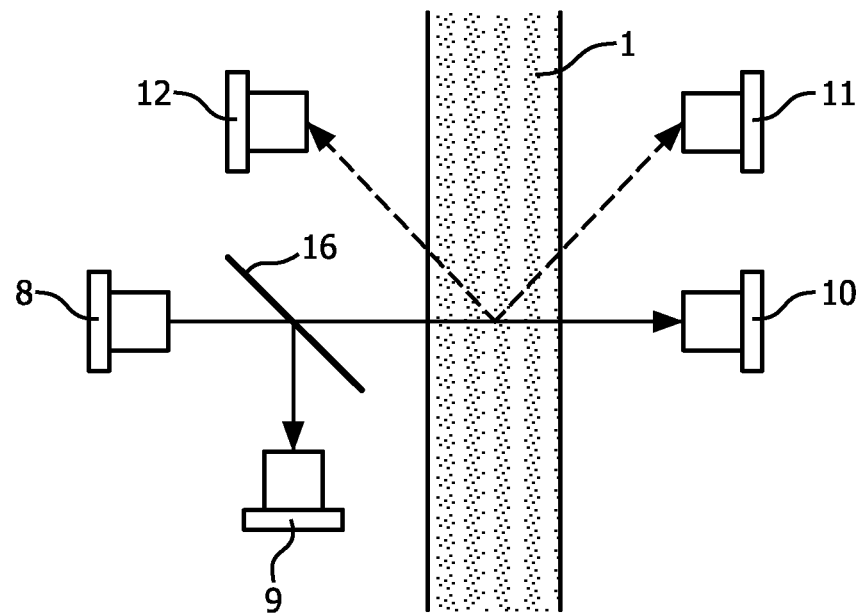
FIG. 3 shows a method comprising a light sources and a plurality of optical sensors located around a fluid flow.

FIG. 3 shows a third embodiment of the method, comprising one light source 8, four optical sensors 9,10,11,12 and a beam splitter 16, arranged around the fluid flow 1. In this embodiment, the light source 8 is a laser diode and the optical sensors 9,10,11,12 are photodiodes. As before, the fluid flow 1 is breast milk expressed from a breast and having entered a breast pump (not shown).

The optical sensors 9,10,11,12 are configured to detect the light scattering rate caused by the fat globules in the breast milk 1—the turbidity of the breast milk 1. Turbidity is an optical characteristic that indicates haziness or cloudiness of a fluid caused by individual particles. It is known to measure the turbidity of a fluid by measuring the attenuation and/or scattering of light, as the light is transmitted through the fluid. As described earlier, breast milk contains fat globules and so the amount of light scattered as the light passes through the breast milk will give a measurement of the fat content of the breast milk. If more fat globules are present, more light will be scattered.

In the embodiment shown in FIG. 3, the laser diode 8 and the beam splitter 16 are configured such that the light emitted from the laser diode 8 is split into two portions, one of which is directed into the first photodiode 9, the other of which is directed towards the flow of breast milk 1. The measurement value of the first photodiode 9, detecting the first part of the split portion of light from the laser diode 8, acts as a control measurement. As the second portion of light interacts with the flow of breast milk 1, some of the light passes through the flow and is detected by the second photodiode 10. The second photodiode 10 is configured to give a measurement of the attenuation of the light, compared to the measurement of the first photodiode 9. The remainder of the light is either absorbed or scattered in any direction. Third and fourth photodiodes 11, 12 are positioned so as to detect light scattered in particular directions. All four photodiodes 9,10,11,12 communicate their measurements to a control unit (not shown) which uses an algorithm, derived from empirical data, to determine the fat content of the breast milk 1. It may achieve this by using the readings in numerous ways. In this embodiment, the turbidity, and therefore fat content, of the breast milk 1 can be determined by comparing the following ratios to each other and to empirically derived constants:

Forward scattering ratio (third photodiode 11/first photodiode 9)

Backward scattering ratio (fourth photodiode 12/first photodiode 9)

Transmitting attenuation ratio (second photodiode 10/first photodiode 9)

It should be noted this embodiment can be simplified, to calculate only one value of the above ratios. Measuring all of them will increase the accuracy.

Figure 4:
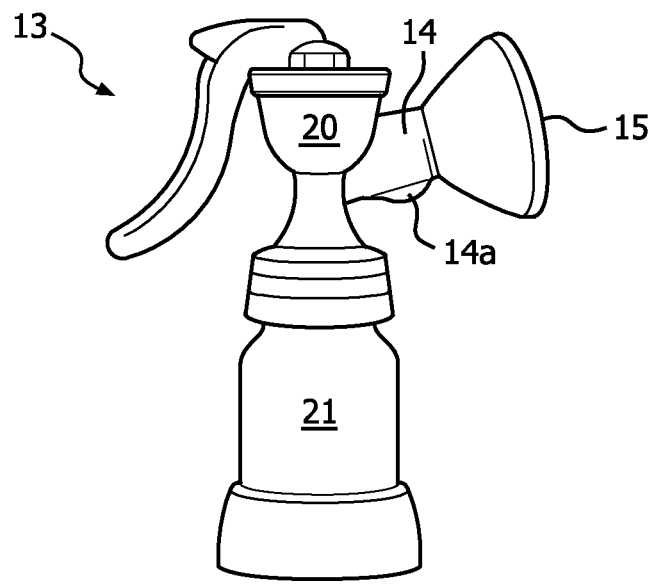
FIG. 4 shows a perspective view of a typical breast pump assembly.

FIG. 4 shows a typical breast pump assembly 13 having a breast receiving shield 15 that narrows to a cylindrical portion 14 which connects the breast receiving shield 15 to the body 20 of the breast pump and a milk collecting container 21. The cylindrical portion 14 may have a deformity, bulge or other formation 14a to which an optical sensor, such as a sensor described with reference to FIGS. 1 to 3 can be attached. This is the preferred location for the sensor, as it is advantageous for the breast milk to be analyzed by the sensor immediately upon, or very shortly after, leaving the breast and before it is mixed with the breast milk already in the milk collecting container 21 to allow changes in breast milk fat content to be detected with the greatest degree of accuracy. The sensors may be removably mounted to the breast pump to allow their removal prior to cleaning of the breast pump.

During pumping, breast milk flows along the cylindrical portion 14 and a sample of it will pass through the deformity or bulge 14a which provides a buffer area because the milk that passes through this region may be less turbulent relative to the milk passing through the cylindrical portion 14, making it easier to analyses. Clearly, if the device for measuring a change in the optical characteristic of the expressed milk is mounted to the outside of the breast shield, then the breast shield, or at least a portion of the breast shield in the vicinity of the bulge 14a, must be formed from a transparent material that will have little or no effect on the light passing through it into the milk being analyzed.

The sensors generate a signal which is fed back to either the user or to a breast pump control unit. A user interface might inform the user when the amount of milk remaining in the breast is low or empty. For example, a series of lights or other indicia may be displayed to indicate the amount of milk remaining in the breast based on the determined measurements. Whether or not the breast pump is provided with a user interface, the breast pump control unit might use the measurements to determine if the pumping power is sufficient and to increase or decrease the power as appropriate. It may also automatically stop pumping if the measurements indicate that the breast is empty or only a small amount of milk remains in the breast.

Although each of the methods for providing an indication as to the amount of milk remaining in a breast during lactation have been described separately, it will be appreciated that it is also possible to use any combination of methods simultaneously to achieve a more accurate and reliable measurement.

It will be appreciated that the term "comprising" does not exclude other elements or steps and that the indefinite article "a" or "an" does not exclude a plurality. The mere fact that certain measures are recited in mutually different dependent claims does not indicate that a combination of these measures cannot be used to an advantage. Any reference signs in the claims should not be construed as limiting the scope of the claims.

Although claims have been formulated in this application to particular combinations of features, it should be understood that the scope of the disclosure of the present invention also includes any novel features or any novel combinations of features disclosed herein either explicitly or implicitly or any generalization thereof, whether or not it relates to the same invention as presently claimed in any claim and whether or not it mitigates any or all of the same technical problems as does the parent invention. The applicants hereby give notice that new claims may be formulated to such features and/or combinations of features during the prosecution of the present application or of any further application derived therefrom.

Other modifications and variations falling within the scope of the claims hereinafter will be evident to those skilled in the art.

The invention claimed is:

1. A method of providing an indication as to the amount of milk remaining in a breast during lactation based on a determined fat content of milk that has been expressed from said breast, wherein the method of determining said fat content comprises measuring, via a sensor, an optical characteristic of milk during expression and by comparing via a control unit, said measured optical characteristic with data representing a corresponding optical characteristic of a sample of milk having a known fat content to determine the fat content of said expressed milk, determining, via said control unit, in real time during lactation an indication of the amount of milk remaining in the breast from the determined fat content of said expressed milk, and supplying a signal representative of the determined fat content of the expressed milk to said control unit, said control unit being operable to automatically control pumping in dependence on said signal.

2. A method according to claim 1, wherein the method includes the step of applying an algorithm to determine the fat content of expressed milk based on said comparison of the measured optical characteristic and said corresponding optical characteristic of a sample of milk having a known fat content to determine the fat content of said expressed milk.

3. A method according to claim 1 wherein the step of measuring an optical characteristic of the expressed milk comprises the step of illuminating a portion of milk using a light source and using an RGB sensor to detect the color of the expressed milk and subsequently comparing said measured color with the color of a sample of milk having a known fat content to determine the fat content of said expressed milk which is indicative of the amount of milk remaining in the breast.

4. A method according to claim 1, wherein the step of measuring an optical characteristic of the expressed milk comprises the step of illuminating milk following expression using a light source and using said sensor to detect the amount of light that is absorbed by said expressed milk, and subsequently comparing said measured absorption with data representing the absorption of a sample of milk having a known fat content to determine the fat content of said expressed milk which is indicative of the amount of milk remaining in the breast.

5. A method according to claim 4, wherein the step of using said sensor to detect the amount of light that is absorbed by the expressed milk comprises the step of illuminating the expressed milk with light of a predetermined wavelength and which is known to be scattered or absorbed by globules of fat contained in expressed milk, detecting the amount of light transmitted through said milk and comparing said measured amount of transmitted light with data representing the amount of light transmitted through a sample of milk having a known fat content to determine the fat content of said expressed milk which is indicative of the amount of milk remaining in the breast.

6. A method according to claim 5, wherein the method includes the step of illuminating a portion of expressed milk with multiple light sources that emit light of different wavelengths and using multiple sensors to detect the amount of light of each wavelength that is transmitted through the expressed milk, and comparing said measured amount of transmitted light with the amount of light transmitted through a sample of milk having a known fat content to determine the fat content of said expressed milk which is indicative of the amount of milk remaining in the breast.

7. A method according to claim 1 wherein the step of measuring an optical characteristic of the expressed milk comprises the step of illuminating a portion of expressed milk using a light source and using said sensor to detect attenuation of the light by said expressed milk, and subsequently comparing said measured attenuation with data representing the attenuation of a sample of milk having a known fat content to determine the fat content of said expressed milk which is indicative of the amount of milk remaining in the breast.

8. A method according to claim 7, comprising multiple sensors to detect light transmitted through the expressed milk and light which is scattered by said expressed milk and comparing the detected light with light received by a control detector that has not been incident on the expressed milk.

9. A method for analyzing breast milk according to claim 8, including the step of providing a beam splitter positioned in the path of the light emitted from the light source such that a portion of the light emitted therefrom towards the expressed milk is directed towards the control detector.

10. A method according to claim 1, comprising the step of informing the user of the determined fat content of the expressed milk or other indicia representative of the amount of milk remaining in said breast based on the determined fat content, such that the user may control pumping in dependence on said information.

11. A breast pump comprising: a detection unit configured to provide an indication as to the amount of milk remaining in a breast during lactation based on a determined fat content of milk that has been expressed from said breast, said detection unit comprising a light source and a sensor configured to detect an optical characteristic of milk as it is expressed from a breast during lactation, said detection unit being releasably attachable to the breast pump and operable to measure said optical characteristic and compare said measured optical characteristic with a corresponding optical characteristic of a sample of milk having a known fat content to determine the fat content of said expressed milk and determine in real time during lactation an indication of the amount of milk remaining in the breast from the determined fat content of said expressed milk, wherein said sensor is configured to generate a signal representative of the determined fat content of the expressed milk, and a control unit being operable to automatically control pumping of said breast pump in response to said signal generated by said sensor.

12. A breast pump according to claim 11, wherein said breast pump comprises a breast shield for insertion of a breast into the breast pump during use, said detection unit being releasably attachable to said breast shield.

13. A breast pump according to claim 12, wherein the breast shield has a bulge or recess therein to receive and temporarily retain or buffer a sample of milk, said detection unit being operable to measure an optical characteristic of the milk in said bulge or recess when said detection unit is attached to said breast pump.

* * * * *